United States Patent [19]

Friese

[11] Patent Number: 4,649,201

[45] Date of Patent: Mar. 10, 1987

[54] REMOVAL OF FERRIC CHLORIDE FROM HALOPYRIDINES

[75] Inventor: David D. Friese, Concord, Calif.

[73] Assignee: The Dow Chemical Company, Midland, Mich.

[21] Appl. No.: 813,905

[22] Filed: Dec. 27, 1985

[51] Int. Cl.[4] .................... C07D 211/60; C01G 3/00
[52] U.S. Cl. .................... 546/345; 546/346; 423/493
[58] Field of Search ............... 546/345, 346; 423/493

[56] References Cited

U.S. PATENT DOCUMENTS

| | | | |
|---|---|---|---|
| 3,538,100 | 11/1970 | Smith | 546/345 |
| 4,225,718 | 9/1980 | Perettie et al. | 546/345 |
| 4,256,894 | 3/1981 | Dietsche et al. | 546/345 |
| 4,542,221 | 9/1985 | Jones | 546/345 |
| 4,546,192 | 10/1985 | Fujioka et al. | 546/345 |

FOREIGN PATENT DOCUMENTS 110690  6/1984  European Pat. Off. ............ 546/345

*Primary Examiner*—Henry R. Jiles
*Assistant Examiner*—Robert C. Whittenbaugh
*Attorney, Agent, or Firm*—D. Wendell Osborne

[57] ABSTRACT

Ferric chloride is removed from mixtures with chlorinated and/or fluorinated pyridines and methylpyridines by extraction with diol solvents. For example, the ferric chloride in halopyridine mixtures containing 2,3,5,6-tetrachloropyridine was removed by extraction with ethylene glycol. The purified halopyridines are useful intermediates for the production of insecticides, herbicides, and fungicides.

16 Claims, No Drawings

REMOVAL OF FERRIC CHLORIDE FROM HALOPYRIDINES

BACKGROUND OF THE INVENTION

The use of ferric chloride as a catalyst in chlorination and fluoride-chloride exchange reactions involving halopyridines is well known and ferric chloride is a common component of reaction mixtures obtained in the manufacture of halopyridines. For example, ferric chloride is a catalyst for the preparation of 2,3,5,6-tetrachloropyridine by chlorination of 2,6-dichloro-pyridine (U.S. Pat. No. 3,538,100), 3,5-dichloro-pyridine (U.S. Pat. No. 4,225,718), or 2-chloro-6-(trichloromethyl)-pyridine (U.S. Pat. No. 4,256,894); the preparation of 2,3-dichloro-6-(trichloromethyl)-pyridine by chlorination of 2-chloro-6-(trichloromethyl)-pyridine (U.S. Pat. No. 4,256,894); the preparation of 3,5-dichloro-2,4,6-trifluoropyridine by halogen exchange of pentachloropyridine (U.S. Pat. No. 4,542,221) and the preparation of 2,3-dichloro-5-(trifluoromethyl)-pyridine by halogen exchange of 2,3-dichloro-5-(tri-chloromethyl)-pyridine (EPO Application No. 83307212.7) or 2-fluoro-3-chloro-5-(trifluoromethyl)pyridine (U.S. Pat. No. 4,546,192). Additionally, ferric chloride is commonly present as an undesirable corrosion product in such reactions. This ferric chloride must generally be removed from the halopyridine in a purification procedure before the halopyridine can be sold or utilized as an intermediate for the preparation of other useful products.

Ferric chloride is conventionally removed from halopyridine and other halogenated compound mixtures containing it by distillation, which leaves the ferric chloride as a non-distillable residue, or by dissolving the halogenated compound in a chlorinated hydrocarbon solvent, which leaves the ferric chloride as a solid that can be separated by filtration. Neither of these methods is very efficient and their utility in commercial operations is limited. This is because halopyridines appear to bond to ferric chloride in some manner and this bonding results not only in a high apparent solubility of ferric chloride in halopyridines, but also in a difficulty in separating them. Thus, even though it is possible and often desirable to isolate the bulk of a halopyridine from a mixture by distillation, distillation alone is not efficient because after completion of the distillation much of the halopyridine remains in the residue with the ferric chloride and cannot be separated from the ferric chloride by further distillation. Heating to higher temperatures causes decomposition of halopyridines and is therefore wasteful and dangerous. Extraction of ferric chloride contaminated halopyridines with chlorinated hydrocarbon solvents is also not efficient as that portion of the halopyridine bound to ferric chloride is not extracted. Additionally, the chlorinated hydrocarbon solvent employed must be removed from the halopyridine in a subsequent operation. This situation and the high value of many halopyridines makes it desirable to have improved methods of separating ferric chloride from halopyridines.

SUMMARY OF THE INVENTION

It has now been found that ferric chloride can be extracted from its mixtures with halopyridines using certain immiscible diol solvents. Ferric chloride is soluble in these diol solvents and is removed from the mixture as a solution in them, leaving the essentially ferric chloride free halopyridine as a residue. An important additional benefit of the process is that much of the by-product tarry material often present in halopyridine reaction mixtures is extracted from the desired halopyridines as well.

The ferric chloride removal process of the present invention is effected by admixing a liquid mixture containing ferric chloride and at least one halopyridine compound of the formula

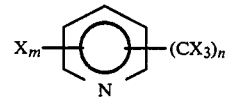

wherein
each X, independently, represents chlorine or fluorine,
m represents an integer of 1 to 5, and
n represents an integer of 0 to 2 with the proviso that the sum of m and n is an integer of 2 to 5,
with an immiscible diol solvent of the formula

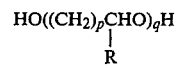

wherein
R represents hydrogen or methyl,
p represents an integer of 1 or 2, and
q represents an integer of 1 to 4,
allowing the admixture to separate into halopyridine and diol solvent phases; and, thereafter, removing the diol phase from the halopyridine phase.

The process of the present invention has been found to be very efficient. Up to 99 percent recovery of halopyridines, which originally contained up to 20 percent ferric chloride and after extraction contained less than one percent, has been achieved. The halopyridines extracted using the process of the present invention generally contain less than 0.5 percent residual diol solvent. They can be used directly for many applications; can be further purified by conventional techniques, such as distillation or crystallization; or can be recycled back into the process from which they were derived.

The purified halopyridines of the present invention are useful herbicides and nitrification inhibitors and are useful intermediates for the production of insecticides, fungicides and herbicides.

DETAILED DESCRIPTION OF THE INVENTION

The present process works well for halopyridine mixtures with ferric chloride that contain either predominantly a single halopyridine specie or a composite of halopyridine species, none of which is predominant. The mixtures may also contain other components. Examples of halopyridines which can be present in the halopyridine-ferric chloride mixtures of the invention include pentachloropyridine; 2,3,4,5-, 2,3,4,6-, and 2,3,5,6-tetrachloropyridine; 2,3,5-, and 2,3,6-trichloropyridine, 3,5-dichloro-2,4,6-trifluoropyridine; 3,5-dichloro-2,6-difluoropyridine; tetrachloro-4-(trichloromethyl)pyridine; 2,3,6-trichloro-4-(trichloromethyl)pyridine; 2,6-dichloro-4-(trifluoromethyl)pyridine; tetrachloro-3-(trichloromethyl)pyridine; 2,3,6-trichloro-5-(trichloromethyl)pyridine; 2,3- and 2,6- dichloro-5-(trichloromethyl)pyridine; 2-chloro-5-(trichloromethyl)pyridine; 2,3- and 2,6-dichloro-5-(trifluoromethyl)pyridine; 2,3- and 2,6-dichloro-5-(chlorodifluoromethyl)pyridine; 2-chloro-5-(dichlorofluoromethyl)pyridine, 2-chloro-5-(trifluoromethyl)pyridine; 2-chloro-3-fluoro-5-(trifluoromethyl)pyridine; 3-chloro-2-fluoro-5-(chlorodifluoromethyl)pyridine; 2-fluoro-5-(chlorodifluoromethyl)pyridine; 2,3-difluoro-5-(trifluoromethyl) pyridine; tetrachloro-2-(trichloromethyl)pyridine; 3,4,5- and 3,5,6-trichloro-2-(trichloromethyl)pyridine; 5,6- and 3,6-dichloro-2-(trichloromethyl)pyridine; 3,6-dichloro-2-(trifluoromethyl)pyridine; 3-chloro-2-fluoro-6-(chlorodifluoromethyl)pyridine; 2-chloro-6-(trichloromethyl)pyridine; 2-fluoro-6-(dichlorofluoromethyl)pyridine; 2-chloro-3,5-bis(trichloromethyl)pyridine; 2,6-dichloro-3,5-bis(-trichloromethyl)pyridine and 2-chloro-3,5-bis(trifluoromethyl)pyridine. Such compounds and their methods of preparation are well known in the art.

Diols that are essentially immiscible with the extracted halopyridine containing composition and in which ferric chloride is soluble to some degree are useful solvents in the process. Examples of useful diol solvents include ethylene glycol; propylene glycol; 1,3-propanediol; mono-, di-, tri-, and tetraethylene glycol; mono-, di-, tri-, and tetrapropylene glycol. Ethylene glycol and propylene glycol are preferred. The diols employed are generally items of commerce.

It is essential that the ferric chloride-halopyridine mixtures of the invention be in the liquid state during the extraction operation of the process. Suspended solids may, however, be present. Many such mixtures are liquid at ambient temperatures and can be extracted at these or at elevated temperatures. Solid or semisolid mixtures can be liquified before the extraction operation by heating to temperatures up to 150° C. and/or by the addition of chlorinated hydrocarbon solvents such as methylene chloride, chloroform, carbon tetrachloride, 1,2-dichloroethane, 1,1,1-trichloroethane, trichloroethylene, or tetrachloroethylene. It is preferred to carry out the extraction at temperatures below 130° C. and more preferred below 45° C. If a chlorinated hydrocarbon solvent is added, it is preferred to use as little as possible to effect liquification at the temperature of the extraction.

The ratio of diol solvent to ferric chloride-halopyridine mixture used in the process varies depending on the amount of ferric chloride present, the specific halopyridines present, and the specific diol solvent employed. The process works well with excess diol solvent, but it is economically advantageous to minimize its amount. This minimum amount is sometimes less than the theoretical minimum calculated based on the solubility of ferric chloride in the diol solvent; i.e., ferric chloride is often more soluble in a diol solvent containing materials extracted from the mixture than in pure diol solvent. Ratios of diol solvent to ferric chloride-halopyridine mixture of from about 10 to 1 to about 1 to 50 are usefully employed for mixtures containing about 1 to about 30 percent ferric chloride. Ratios of about 5 to 1 to about 1 to 10 are usually employed.

The process of the invention can be carried out either batchwise or in a continuous manner. For batch operations any vessel equipped with means for adding the halopyridine-ferric chloride mixture and the diol solvent, agitating, heating (if required), and separating the phases can be employed. For continuous operations a counter current flow liquid-liquid column extractor having means for introducing the halopyridine-ferric chloride mixture at the top and removing it at the bottom and means for introducing the immiscible diol solvent at the bottom and removing it at the top, is typically employed. In either system the two phases must be thoroughly mixed to obtain optimal removal of the ferric chloride.

The following examples are merely illustrations of the present invention and should not be construed as limiting.

EXAMPLE 1

2,3,5,6-Tetrachloropyridine Mixture Extraction with Ethylene Glycol

A 19.2 g sample of a mixture having the composition shown in the table below was combined with 27.8 g of ethylene glycol in a jar. The admixture was heated to 125° C. and manually shaken on about 15 minute intervals for about 100 minutes. The phases were allowed to separate and the upper ethylene glycol phase was removed with a pipette. The lower phase containing the halopyridines weighed 17.6 g and was found to have the composition shown in the table below.

| Mixture Component | Initial Conc., % | Final Conc., % |
| --- | --- | --- |
| 2,3,5,6-tetrachloropyridine | 61.6 | 65.5 |
| pentachloropyridine | 15.9 | 17.4 |
| other identifiable chloropyridines | 12.9 | 14.9 |
| Total chloropyridines | 90.4 | 97.8 |
| ferric chloride | 1.6 | <0.4 |
| other non-volatiles | 1.2 | not detectable |
| ethylene glycol | — | not detectable |

Thus, by this analysis, there was over 75 percent reduction in the ferric chloride content with a loss of only about 1 percent of the total chloropyridines.

EXAMPLE 2

3,5,6-Trichloro-2-(trichloromethyl)pyridine Mixture Extraction with Ethylene Glycol.

An 8.56 g sample of a mixture containing 87.4 percent volatile chloropyridines including 3,5,6-trichloro-2-(trichloromethyl)pyridine, 2.2 percent ferric chloride, and 10.4 percent non-volatile tars was combined with 9.91 g of ethylene glycol in a jar at 22° C. The admixture was shaken manually every 15 minutes for several hours and then allowed to separate into phases, both of which were very dark. The top ethylene glycol phase was removed as well as possible with a pipette. The lower halopyridine phase, which was an estimated 7.8 g, contained about 96 percent volatile chloropyridines including 3,5,6-trichloro-2-(trichloromethyl)pyridine, any residual ethylene glycol, about 1 percent ferric chloride, and about 3.3 percent non-volatile tars.

EXAMPLE 3

2,3-Dichloro-5-(trihalomethyl)pyridine Mixture Extraction with Ethylene Glycol

Ethylene glycol (94 parts) was placed in a reaction vessel and a ferric chloride-halopyridine mixture (240 parts) which had been heated to 85° C. was added. The admixture was agitated and allowed to cool to about 52° C. over a 1 hour period. The phases were allowed to separate and cool to 45° C. and the lower halopyridine phase was then removed through a bottom drain. It amounted to 162 parts. Analyses of the ferric chloride-halopyridine mixture before and after extraction is shown in the table below.

| Mixture Component | Initial Conc., % | Final Conc., % |
|---|---|---|
| 2,3-dichloro-5-(trichloromethyl)pyridine | 14.9 | 24.1 |
| 2,3-dichloro-5-(chlorodifluoromethyl)pyridine* | 9.6 | 13.4 |
| 2,3-dichloro-5-(dichlorofluoromethyl)pyridine* | 14.0 | 23.6 |
| 2,3-dichloro-5-(trifluoromethyl)pyridine* | 11.5 | 21.0 |
| other volatile halopyridines | 5.3 | 9.1 |
| Total halopyridines | 55.3 | 91.2 |
| ferric chloride | 20.1 | 1.6 |
| ethylene glycol | — | 0.3 |

*may include isomers

The ferric chloride reduction was about 92 percent and the halopyridine recovery about 90 percent.

I claim:

1. A process for extracting ferric chloride from mixtures comprising ferric chloride and at least one halopyridine compound of the formula

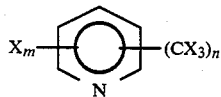

wherein
each X, independently, represents Cl or F,
m represents an integer of 1 to 5, and
n represents an integer of 0 to 2 with the proviso that the sum of m and n is an integer of 2 to 5,
which comprises: admixing the halopyridine as a liquid with an essentially immiscible diol solvent of the formula

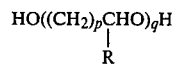

wherein
R represents hydrogen or methyl,
p represents an integer of 1 or 2, and
q represents an integer of 1 to 4;
allowing the admixture to separate into halopyridine and diol solvent phases; and, thereafter, removing the diol solvent phase from the halopyridine phase.

2. A process of claim 1 wherein the diol solvent is ethylene glycol.

3. A process of claim 1 wherein the diol solvent is propylene glycol.

4. A process of claim 1 wherein the extraction is conducted batchwise.

5. A process of claim 1 wherein the extraction is conducted in a continuous manner.

6. A process of claim 1 wherein the mixture is made liquid by heating.

7. A process of claim 1 wherein the mixture is made liquid by the addition of a chlorinated hydrocarbon solvent.

8. A process of claim 1 wherein the halopyridine compound is 2,3,5,6-tetrachloropyridine.

9. A process of claim 1 wherein the halopyridine compound is 3,5-dichloro-2,6-difluoropyridine.

10. A process of claim 1 wherein the halopyridine compound is 2,3-dichloro-5-(trichloromethyl)pyridine.

11. A process of claim 1 wherein the halopyridine compound is 2,3-dichloro-5-(chlorodifluoromethyl)pyridine or 2-fluoro-3-chloro-5-(dichlorofluoromethyl)pyridine.

12. A process of claim 1 wherein the halopyridine compound is 2,3-dichloro-5-(trifluoromethyl)pyridine.

13. A process of claim 1 wherein the halopyridine compound is 2-chloro-5-(trifluoromethyl)pyridine.

14. A process of claim 1 wherein the halopyridine compound is 2,3-difluoro-5-(trifluoromethyl)pyridine.

15. A process of claim 1 wherein the halopyridine compound is 3,6-dichloro-2-(trichloromethyl)pyridine.

16. A process of claim 1 wherein the halopyridine compound is 2,3,5-trichloro-6-(trichloromethyl)pyridine.

* * * * *